United States Patent [19]

Miller

[11] Patent Number: 4,495,662
[45] Date of Patent: Jan. 29, 1985

[54] NIGHTTIME GARMENT FOR OSTOMY POUCH USER

[76] Inventor: Janine Miller, 43 Ardale Rd., Paramus, N.J. 07652

[21] Appl. No.: 423,161

[22] Filed: Sep. 24, 1982

[51] Int. Cl.³ .................. A41D 1/14; A41D 27/20; A61F 5/44
[52] U.S. Cl. .................................. 2/211; 2/252; 604/332
[58] Field of Search .............. 2/249, 211, 69, 252, 2/221; 128/283, 286, 295, 275, DIG. 7

[56] References Cited

U.S. PATENT DOCUMENTS

| | | | |
|---|---|---|---|
| 604,964 | 5/1898 | Cain | 2/211 |
| 1,264,445 | 4/1918 | Schwieger | 2/211 |
| 1,458,319 | 6/1923 | Bemis | 2/247 |
| 1,793,737 | 2/1931 | Estes | 2/211 |
| 3,065,471 | 11/1962 | Leu | 2/113 |
| 3,230,545 | 1/1966 | Galley | 2/74 |

*Primary Examiner*—Doris L. Troutman
*Attorney, Agent, or Firm*—Samuelson & Jacob

[57] ABSTRACT

A nighttime garment to be worn by a person for concealing an ostomy pouch used by the person, the garment including a decorative wrap-around skirt-like member having an inner pocket for receiving the ostomy pouch for concealment behind the skirt-like member, and a securing arrangement enabling adjustment of the skirt-like member for waist size and for location of the ostomy pouch.

9 Claims, 4 Drawing Figures

NIGHTTIME GARMENT FOR OSTOMY POUCH USER

The present invention relates generally to decorative garments and pertains, more specifically, to a nighttime garment to be worn by a person who uses an ostomy pouch, for the purpose of concealing the ostomy pouch behind an aesthetically attractive garment.

Many surgical garments have been made available for use with ostomy pouches. Most of these garments are strictly functional and are aesthetically rather unpleasant. Recent advances in ostomy appliances such as ileostomy, colostomy and urostomy pouches now enable the use of more simplified and less obtrusive ostomy pouches; nevertheless, the pouches themselves, and their attachment, can be a source of aesthetic displeasure, especially to feminine users of ostomy pouches. This is true particularly in the case of nighttime wear when only minimal support is required for the ostomy pouch and aesthetic appearance can be an important consideration.

It is an object of the present invention to make available a garment for users of ostomy pouches, the garment providing an aesthetically pleasing appearance especially suited to nighttime wear.

Another object of the invention is to make available a garment of the type described and which provides a relatively simple arrangement for concealing an ostomy pouch used by the wearer.

Still another object of the invention is to make available a garment of the type described and which is adjusted readily for size and for the accommodation of different locations of an ostomy pouch.

Yet another object of the invention is to provide a garment of the type described and which is easy to use and to care for.

A further object of the invention is to provide a garment of the type described and which is economically fabricated of readily-available materials.

A still further object of the invention is to make available a garment of the type described and which is decorative and finds widespread appeal, particularly among feminine users of ostomy pouches.

The above objects, as well as still further objects and advantages, are attained by the present invention which may be described briefly as a nighttime garment to be worn by a person for concealing an ostomy pouch used by the person, the garment comprising: a wrap-around skirt-like member including a waist portion and a depending skirt portion, the skirt portion having an inner surface and an opposite outer surface; a pocket on the inner surface; securing means at the waist portion for securing the skirt-like member at the waist of the person, with the skirt-like member wrapped around the person, the inner surface confronting the person, and the pocket juxtaposed with the ostomy pouch; an opening in the pocket for passing the ostomy pouch therethrough; and a closure for selectively closing at least a portion of the opening for securing the ostomy pouch within the pocket, concealed behind the outer surface of the skirt portion.

The invention will be more fully understood, while still further objects and advantages will become apparent, in the following detailed description of a preferred embodiment thereof illustrated in the accompanying drawing, in which.

Figure 1:
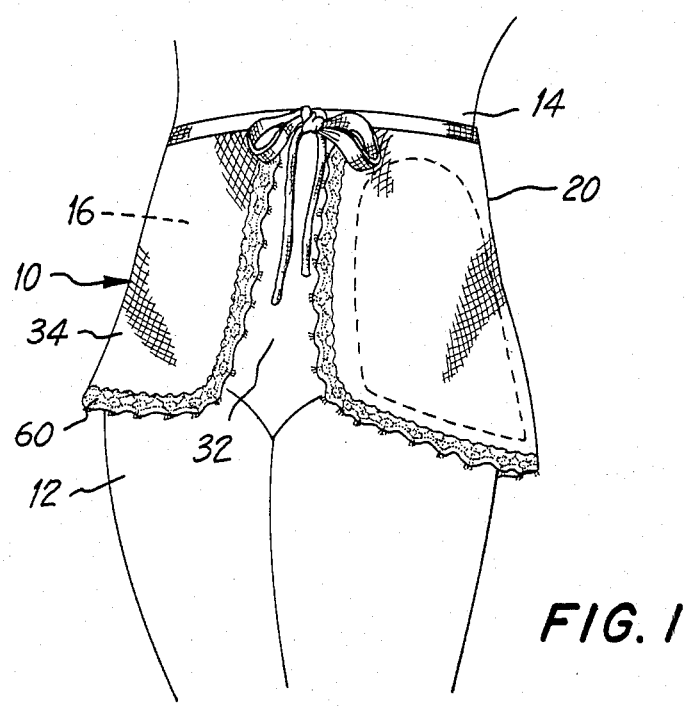
FIG. 1 is a pictorial view illustrating a garment constructed in accordance with the invention in place upon a wearer.

Referring now to the drawing, and especially to FIG. 1 thereof, a garment constructed in accordance with the invention is illustrated generally at 10 and is shown in place upon a wearer 12. Garment 10 is a skirt-like garment secured around the waist 14 of the wearer 12 and generally covering the lower portion 16 of the torso of the wearer. The wearer 12 uses an ostomy pouch shown in the form of an ileostomy pouch which is concealed behind the garment 10. In this instance, the ileostomy pouch is located at the left side of the user.

Figure 2:
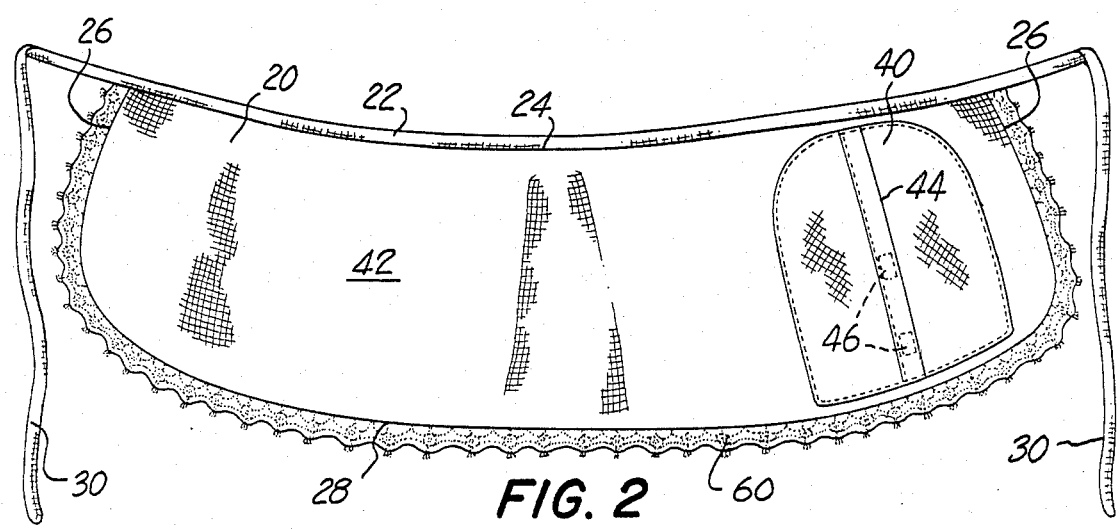
FIG. 2 is a plan view of the garment.

Turning now to FIG. 2, garment 10 includes a panel 20 of material establishing a skirt-like portion of the garment which depends downwardly from a waist portion, shown in the form of a waist band 22 sewn along the upper edge 24 of the panel 20. The peripheral edge of panel 20 further includes vertical lengths at vertical edges 26 spaced apart horizontally and interconnected by a horizontal length along horizontal edge 28, the vertical and horizontal edges forming the perimeter of the skirt-like portion.

The waist band 22 terminates in ties 30 which serve as securing means when tied about the waist 14 of the wearer 12, as seen in FIG. 1. The ties 30 render the securement adjustable for waist size; that is, panel 20 may be wrapped about the torso of the wearer 12 to fit the particular waist size of the wearer, with the spacing 32 between vertical edges 26 being variable, depending upon a given size, to accommodate a range of sizes, and with outer surface 34 of panel 20 exposed to view.

In order to provide support for the ileostomy pouch, a pocket 40 is sewn onto the inner surface 42 of panel 20. The pocket preferably is located adjacent one or the other of the vertical edges 26 so that upon appropriate arrangement of the garment 10 upon the wearer 12, as will be described in greater detail below, the vertical edges 26 are located generally symmetrically about the center of the wearer, for greater aesthetic effect, as seen in FIG. 1. An opening 44 in the pocket 40 extends in a generally vertical direction along essentially the entire vertical length of the pocket. A closure, here shown in the form of selectively opened Velco fasteners 46, selectively opens and closes the lower portion of opening 44, for purposes which now will be described.

Figure 3:
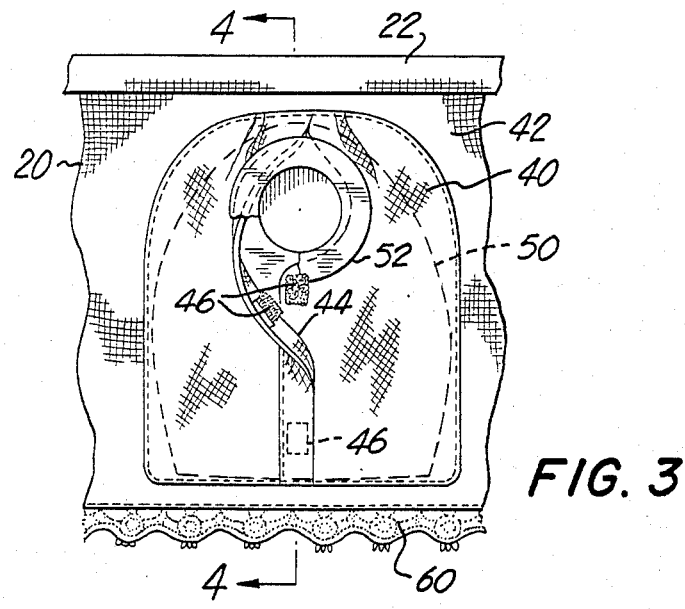
FIG. 3 is an enlarged fragmentary view of a portion of the garment showing the pocket in use.
Figure 4:
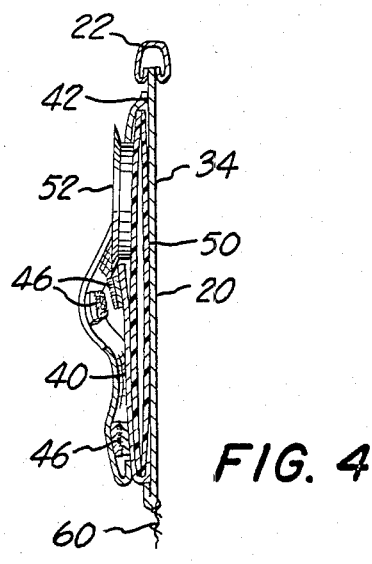
FIG. 4 is a cross-sectional view taken along line 4—4 of FIG. 3.

Referring to FIGS. 3 and 4, as well as to FIGS. 1 and 2, the garment 10 is secured in place over the lower portion 16 of the torso of the wearer 12 so that the pocket 40 is juxtaposed with the ileostomy pouch, illustrated at 50, which is in place on the wearer 12. Garment 10 is supplied in either "left-hand" or "right-hand" versions, depending upon the location of pocket 40, for use by persons having a left or a right ostomy location. The ability to adjust the ties 30 enables the proper placement of the pocket 40 in juxtaposition with the ileostomy pouch 50 when the inner surface 42 of panel 20 confronts the wearer 12, as well as enabling adjustments for size. Fasteners 46 are opened to open the opening 44 so that ileostomy pouch 50 may be passed through opening 44 and into pocket 40. Once the ileostomy pouch 50 is received within pocket 40, fasteners 46 are closed to close the lower portion of opening 44, while the neck 52 of the ileostomy pouch 50 projects through the upper portion 54 of opening 44. Thus, ileostomy pouch 50 is admitted readily into pocket 40 and is securely supported therein, concealed behind panel 20. When it is desired to remove garment 10, the fasteners 46 are opened and ileostomy pouch 50 readily is passed out of the pocket 40 through opening 40.

Garment 10 is fabricated readily of a variety of suitable materials. Preferably, panel 20 is constructed of a polyester knit material which is form-fitting and easily cared for. Such materials are aesthetically pleasing and are enhanced readily, such as by the addition of a decorative border 60 along the vertical and horizontal edges 26 and 28. In the illustrated embodiment, border 60 is in the form of a lace-like material for enhanced appearance. Pocket 40 may be constructed of the same material as panel 20; however, the knit preferably is oriented on the bias so as to provide greater resilience, or stretch, for accommodating the ileostomy pouch 50, as the pouch fills.

The use of ties 30 is a simple and convenient arrangement by which the garment 10 is secured, with adjustments for size and for placement of the pocket 40. However, other securing arrangements will occur to those skilled in the art. For example, various fasteners such as snaps or Velcro fasteners may be employed; however, ties 30 are simple, inexpensive and, as can be seen in FIG. 1, aesthetically pleasing. In addition, the size, configuration and location of pocket 40 may be varied to accommodate the size, configuration and location of an ostomy pouch used by a particular wearer.

Once in place, garment 10 provides an aesthetically pleasing arrangement by which ileostomy pouch 50 is concealed. The outer surface 32 is essentially uninterrupted by any major structure which would reveal the fact that an ileostomy pouch is concealed behind the panel 20. The garment 10 itself is quite feminine in appearance and makes available a decorative arrangement for persons who must use an ostomy pouch.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. A nighttime garment to be worn by a person for concealing an ostomy pouch used by the person, the ostomy pouch having a neck, the garment comprising:
   a wrap-around skirt-like member including a waist portion and a depending skirt portion, the skirt portion having an inner surface and an opposite outer surface;
   a pocket on the inner surface;
   securing means at the waist portion for securing the skirt-like member at the waist of the person, with the skirt-like member wrapped around the person, the inner surface confronting the person, and the pocket juxtaposed with the ostomy pouch;
   an opening in the pocket for passing the ostomy pouch therethrough; and
   a closure for selectively closing at least a portion of the opening, while a further portion of the opening remains unclosed, for securing the ostomy pouch within the pocket, concealed behind the outer surface of the skirt portion, with the ostomy pouch resting in the pocket and the neck of the ostomy pouch extending through the unclosed further portion of the opening.

2. The invention of claim 1 wherein the securing means includes adjustable means for adjustment of the waist size of the garment while enabling the positioning of the pocket in juxtaposition with the ostomy pouch.

3. The invention of claim 2 wherein the securing means includes ties extending from the waist portion.

4. The invention of claim 1 wherein the garment is disposed generally horizontally around the person when secured in place and the opening in the pocket extends in a generally vertical direction.

5. The invention of claim 4 wherein the opening extends along essentially the full vertical extent of the pocket.

6. The invention of claim 5 wherein the closure includes a detachable fastener, such as a Velcro fastener.

7. The invention of claim 1 wherein the skirt portion includes a peripheral edge having horizontally spaced apart vertical edge portion interconnected by a horizontal edge portion and the pocket is located adjacent one of the vertical edge portions.

8. The invention of claim 1 wherein the pocket is constructed of a knitted material affixed to the skirt portion with the knit oriented on the bias for enhanced accommodation of the ostomy pouch received therein.

9. The invention of claim 1 wherein the skirt portion includes a peripheral edge having horizontal spaced apart vertical edge portions interconnected by a horizontal edge portion and a decorative border extending along the peripheral edge.

* * * * *